(12) United States Patent
Smith et al.

(10) Patent No.: US 7,262,151 B2
(45) Date of Patent: Aug. 28, 2007

(54) METHODS AND COMPOSITIONS FOR PRODUCTION OF LIPO-CHITO OLIGOSACCHARIDES BY RHIZOBACTERIA

(75) Inventors: Donald L. Smith, Ste-Anne-de-Bellevue (CA); Fazli Mabood, Ste-Anne-de-Bellevue (CA); Hao Zhang, San Diego (CA)

(73) Assignee: McGill University, Montreal, Quebec (CA)

( * ) Notice: Subject to any disclaimer, the term of this patent is extended or adjusted under 35 U.S.C. 154(b) by 0 days.

(21) Appl. No.: 10/146,034

(22) Filed: May 16, 2002

(65) Prior Publication Data

US 2003/0096375 A1  May 22, 2003

Related U.S. Application Data

(60) Provisional application No. 60/303,037, filed on Jul. 6, 2001.

(51) Int. Cl.
*A01N 63/00* (2006.01)
*C12P 19/44* (2006.01)

(52) U.S. Cl. ............... 504/117; 435/252.2; 424/93.4

(58) Field of Classification Search ............ 435/74, 435/72, 84, 252.2; 424/93.4; 504/117
See application file for complete search history.

(56) References Cited

U.S. PATENT DOCUMENTS 5,549,718 A * 8/1996 Lerouge et al. ............ 47/57.6
5,922,316 A   7/1999 Smith et al.
5,935,809 A   8/1999 Ryan et al.

FOREIGN PATENT DOCUMENTS

| CA | 2243669 | 1/2000 |
|----|---------|--------|
| CA | 2285727 | 4/2001 |
| WO | 00/04778 | 2/2000 |
| WO | 01/26465 A1 | 4/2001 |

OTHER PUBLICATIONS

Rosas, Susana et al., "Jasmonic acid stimulates the expression of *nod* genes in *Rhizobium*", Plant Molecular Biology (1998), 1161-1168.
Ortel, B., "Jasmonate-induced gene expression of barley (*Hordeum vulgare*) leaves—the link between jasmonate and abscisic acid", Plant Growth Regulation (1999), 29:113-122.
Mabood, Fazli, Jasmonates induce the expressoin of *nod* genes in *Bradyrhizobium japonicum*, May 17, 2001.
Mabood, Fazli, Linoleic and linolenic acid induce the expression of *nod* genes in *Bradyrhizobium japonicum* USDA 3, May 17, 2001.

* cited by examiner

*Primary Examiner*—Leon B. Lankford, Jr.
*Assistant Examiner*—Susan Hanley

(57) ABSTRACT

Lipo-chito oligosaccharides (LCOs) are produced by culturing rhizobacteria cells in or on a culture medium comprising at least one of: jasmonic acid or a derivative thereof; linoleic acid or a derivative thereof; or linolenic acid or a derivative thereof. Preferably, the rhizobacteria cells are *Bradyrhizobium japonicum* cells having the identifying characteristics of *B. japonicum* strain USDA 3. Preferably, the derivative of jasmonic acid is an ester thereof, preferably methyl jasmonate. Also provided are methods for improving LCO production at low temperatures, particularly temperatures below 25° C.

20 Claims, 6 Drawing Sheets

METHODS AND COMPOSITIONS FOR PRODUCTION OF LIPO-CHITO OLIGOSACCHARIDES BY RHIZOBACTERIA

CROSS-REFERENCE TO RELATED APPLICATIONS

This application claims the benefit of U.S. provisional application Ser. No. 60/303,037, filed Jul. 6, 2001, which is incorporated herein by reference.

FIELD OF THE INVENTION

The invention relates to the field of microbiology, more particularly to the production of lipo-chito oligosaccharides by rhizobacteria.

BACKGROUND OF THE INVENTION

The symbiotic relationship between leguminous plants and nitrogen-fixing bacteria involves nodule formation. Nodule formation is a complex process requiring communication between the bacteria and the host plant. During the initial events of symbiosis, plant-to-bacteria signal molecules known as flavonoids are produced by the host plant at low concentrations.

The flavonoids induce the expression of nod genes in the rhizobacteria bacteria. The first level of host specificity in the rhizobacteria-legume interaction is modulated by nodD and its alleles. These regulate the transcription of nodulation genes (nod, nol and noe). The nodD gene product, NodD, acts as a sensor of the plant signal and also regulates transcriptional regulation of the nod genes. The bacterial nod, nol and noe genes are required for infection and nodule formation.

Generally, the transcription of nol/noe genes is induced in the presence of NodD and flavonoids produced by host plants. NodD proteins belong to the LysR family of transcriptional activators. In the presence of flavonoids, NodD proteins bind to a nod box, a conserved promoter sequence preceding the inducible nod genes, and activate the transcription of nod operons.

Expression of the nod genes in the rhizobacteria is believed to be involved in the synthesis of lipo-chito oligosaccharides (LCOs). LCOs are substituted, β1,4 linked trimers, tetramers, and pentamers of N-acetylglucosamine. The LCOs, often described as "nod factors", signal the plant and stimulate the formation of nodules inside the host plants.

Successful colonization of legume plants by nitrogen-fixing rhizobacteria is of significant agricultural and commercial importance. It would be particularly useful to obtain sources of LCOs that could be used to promote nodule formation by rhizobacteria. It would also be of benefit to identify compounds that are useful for inducing nod gene expression in rhizobacteria, resulting in production of LCOs. Rhizobacteria strains that are particularly responsive to nod gene induction, and which produce high levels of LCOs would also be of great utility.

A number of flavonoids which induce nod gene expression in rhizobacteria are known. Isoflavones, primarily genistein and diadzein, are the best inducers of nod::lacZ translational fusions and of the nod YABCUIJ operon in *Bradyrhizobium japonicum*. Genistein ($C_{15}H_{10}O_5$, 5,7,4'-trihydroxyisoflavone, MW 270.2) is a stronger inducer of nod genes in *B. japonicum* than diadzein.

Jasmonic acid (JA) (Chemical Abstracts name: [1R-[1α, 2β(Z)]]-3-oxo-2-(pentenyl)cyclopentaneacetic acid) and its methyl ester methyl jasmonate (MeJA), are fatty acid derived molecules. They are octadecanoid-based compounds that occur naturally in plants. Jasmonates are involved in plant growth and development, and play an important role in defence responses against pathogens and in wounding responses.

Jasmonic acid is produced in large quantities by the roots of wheat seedlings, and is also produced by fungal microorganisms such as *Botryodiplodia theobromae* and *Gibbrella fujikuroi*, yeast (*Saccharomyces cerevisiae*), and pathogenic and non-pathogenic strains of *Escherichia coli*. Jasmonic acid plays an important role in mycorrhizal signaling and, when applied to an ectomycorrhizal system, has been shown to increase the number of mycorrhized roots, and shoot and root dry weight of spruce seedlings.

Little is known with respect to how jasmonates affect the growth rate of symbiotic microorganisms, or the activation of bacteria-to-plant signaling molecules (nod factors) or their role in host-specific aspects of symbioses when they are present in the rhizosphere. Rosas et al (1998) recently reported that jasmonic acid and methyl jasmonate induced expression of nod genes in *Rhizobium leguminasorum* strain RBL 1284. However, Rosas et al. (1998) did not report whether jasmonic acid or methyl jasmonate increased LCO production as well.

The first step in jasmonic acid biosynthesis is the formation of linoleic acid (Chemical Abstracts name: (Z,Z)-9,12-Octadecadienoic acid) and linolenic acid (Chemical Abstracts name: (Z,Z,Z)-9,12,15-Octadecatrienoic acid) from membrane lipid breakdown, catalysed by phospholipase. Linoleic and linolenic acid are converted to 13-hydroperoxylinolenic acid by the action of lipoxygenase. 13-hydroperoxylinolenic acid is converted into 12,13 expoxy-octadecatrienoic acid in the presence of allene oxide synthase (AOS), and then converted into 12-oxo-phytodienoic acid by allene oxide cyclase (AOC). Following reduction and three steps of β-oxidation, (+)-7-iso-jasmonic acid is formed.

However, despite the role of linoleic and linolenic acid in the biosynthesis of jasmonic acid, it does not appear that they have been considered as possible inducers of nod gene expression or LCO production by rhizobacteria.

Not only is there a need for methods for increasing LCO production by rhizobacteria, there is a need for methods for increasing LCO production by rhizobacteria at low temperatures, in order to improve symbiotic nitrogen fixing symbiosis of rhizobacteria at low temperatures. Optimal symbiotic activity of rhizobacteria in legumes (i.e. nitrogen fixation) often occurs at a temperature far above that at which legume crops are grown. For instance, soybean is a subtropical legume that requires a root zone temperature ("RZT") in the range of about 25 to 30° C. for optimal symbiotic activity. At low temperatures, expression of nod genes in *B. japonicum*, the soybean nitrogen fixing microsymbiont, are inhibited, resulting in a delayed onset of nodulation. Low spring soil temperature is therefore a major factor limiting soybean growth and symbiotic nitrogen fixation in northern regions, such as in Canada. Hence, methods for improving the symbiotic nitrogen fixing activity of rhizobacteria at low temperatures would be of great benefit to legume crop production in cool climates.

SUMMARY OF THE INVENTION

The inventors have discovered that, surprisingly, jasmonic acid, linoleic acid and linolenic acid are useful for inducing LCO production in rhizobacteria. Derivatives of jasmonic acid, linoleic acid, and linolenic acid, particularly esters, amides, and salts thereof, are also contemplated for use in the present invention. In particular, *Bradyrhizobium japonicum* strain USDA3 is highly responsive to nod gene induction by jasmonic acid esters (jasmonates), resulting in levels of LCO production that are much greater than those obtained from other *B. japonicum* strains. Methyl jasmonate has been determined to be a particularly useful inducer of LCO production in *B. japonicum* strain USDA3.

Thus, in one aspect, the invention provides a method for producing lipo-chito oligosaccharides comprising the steps of culturing rhizobacteria cells in or on a culture medium comprising at least one of: jasmonic acid or a derivative thereof; linoleic acid or a derivative thereof; or, linolenic acid or a derivative thereof; whereby the rhizobacteria cells produce lipo-chito oligosaccharides; and recovering the lipo-chito oligosaccharides from the culture medium.

In another aspect, the invention provides a rhizobial inoculant for promoting nitrogen fixation in legumes at an average root zone temperature below 25° C., the inoculant comprising: (a) rhizobacteria cells; and (b) in an amount sufficient to induce production of lipo-chito oligosaccharides by said rhizobacteria cells, at least one of: jasmonic acid or a derivative thereof; linoleic acid or a derivative thereof; or linolenic acid or a derivative thereof.

In another aspect, the invention provides a method for promoting nitrogen fixation by legumes, comprising inoculating legume plants, seeds, roots, or parts thereof with a rhizobial inoculant as described above, wherein the legume plants are planted under conditions that result in an average daily root zone temperature of less than 25° C.

The invention further provides a kit comprising: a rhizobial inoculant as described above; and instructions for use of the inoculant for inoculating legumes planted under conditions that result in an average daily root zone temperature of less than 25° C.

DETAILED DESCRIPTION OF THE PREFERRED EMBODIMENTS

Figure 1:
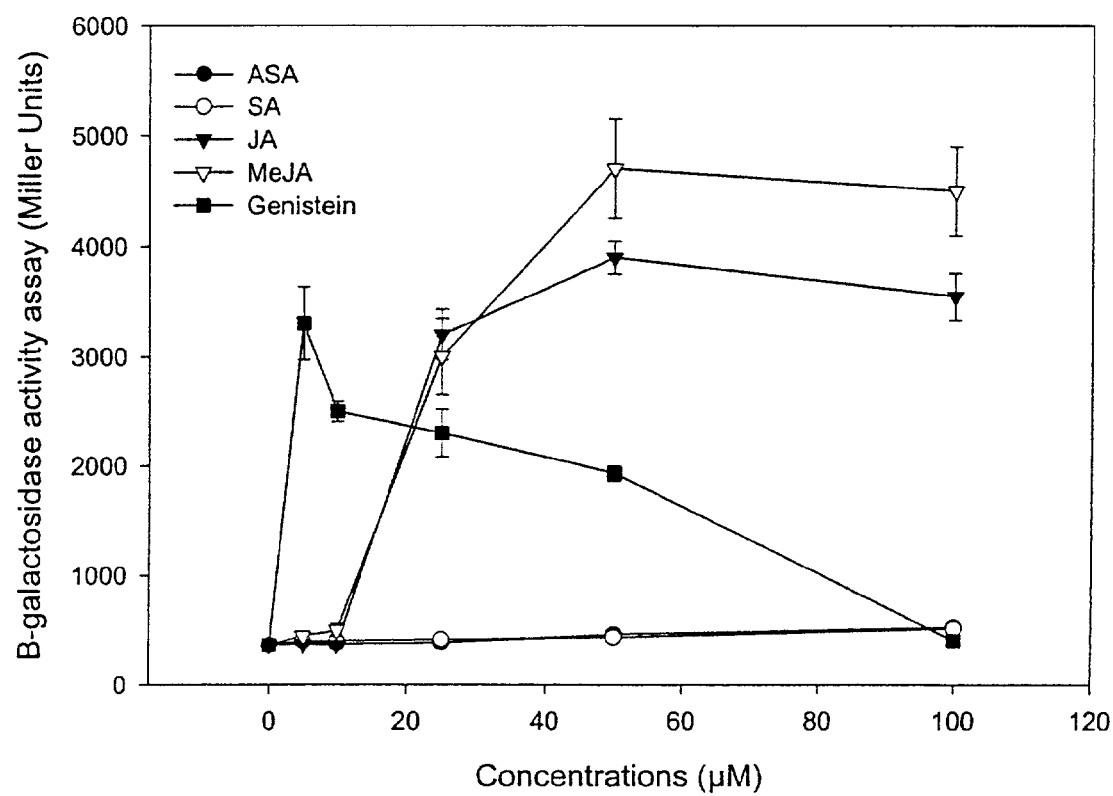
FIG. 1 is a graph depicting the effect of various concentrations of genistein, jasmonic acid, methyl jasmonate, salicylic acid, and acetylsalicylic acid on the induction of nod genes in *Bradyrhizobium japonicum* strain USDA3 as measured by β-galactosidase activity (Miller Units).

In accordance with one aspect of the invention, LCO production by rhizobacteria species is increased by culturing the rhizobacteria in the presence of jasmonic acid, linoleic acid, linolenic acid, or derivatives thereof.

Any rhizobacteria strain useful for increasing nitrogen fixation in leguminous plants finds application in this aspect of the invention. Rhizobacterial strains of interest are bacteria of the family Rhizobiaciae that are able to enter into a symbiotic nitrogen fixing relationship with a leguminous plant, and supply the plant with nitrogen. Most nitrogen fixing rhizobacteria are members of the genera *Bradyrhizobium, Rhizobium, Sinorhizobium,* and *Azorhizobium.* Many suitable nitrogen fixing rhizobacteria are known to the those of skill in the art, and are available commercially, such as *R. meliloti* and *R. leguminosarum,* and rhizobacteria of the genus *Bradyrhizobium.* Preferred strains include those of the species *Bradyrhizobium japonicum,* particularly strain USDA3, exemplified herein, and available from the United States Department of Agriculture or public culture collections.

Useful derivatives of linoleic acid, linolenic acid, and jasmonic acid include, without limitation, esters, amides, glycosides and salts.

Preferred esters are compounds in which the carboxyl group of linoleic acid, linolenic acid, or jasmonic acid has been replaced with a —COR group, where R is an —OR$^1$ group, in which R$^1$ is:

an alkyl group, such as a $C_1$-$C_8$ unbranched or branched alkyl group, particularly a methyl, ethyl or propyl group;

an alkenyl group, such as a $C_2$-$C_8$ unbranched or branched alkenyl group;

an alkynyl group, such as a $C_2$-$C_8$ unbranched or branched alkynyl group;

an aryl group having, for example, 6 to 10 carbon atoms; or a heteroaryl group having, for example, 4 to 9 carbon atoms, wherein the heteroatoms in the heteroaryl group can be, for example, N, O, P, or S.

Preferred amides are compounds in which the carboxyl group of linoleic acid, linolenic acid, or jasmonic acid has been replaced with a —COR group, where R is an

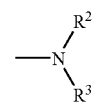

group, in which R$^2$ and R$^3$ are independently:

hydrogen;

an alkyl group, such as a $C_1$-$C_8$ unbranched or branched alkyl group, particularly a methyl, ethyl or propyl group;

an alkenyl group, such as a $C_2$-$C_8$ unbranched or branched alkenyl group;

an alkynyl group, such as a $C_2$-$C_8$ unbranched or branched alkynyl group;

an aryl group having, for example, 6 to 10 carbon atoms; or a heteroaryl group having, for example, 4 to 9 carbon atoms, wherein the heteroatoms in the heteroaryl group can be, for example, N, O, P, or S.

Esters may be prepared by known methods, such as acid-catalyzed nucleophilic addition, wherein the carboxylic acid is reacted with an alcohol in the presence of a catalytic amount of a mineral acid.

Amides may also be prepared by known methods, such as by reacting the carboxylic acid with the appropriate amine in the presence of a coupling agent such as dicyclohexyl carbodiimide (DCC), under neutral conditions.

Suitable salts of linoleic acid, linolenic acid, and jasmonic acid include e.g. base addition salts. The bases that may be used as reagents to prepare metabolically acceptable base salts of these compounds include, but are not limited to those derived from cations such as alkali metal cations (e.g., potassium and sodium) and alkaline earth metal cations (e.g., calcium and magnesium).

These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Jasmonic acid can be used in this invention as a racemic mixture (i.e. as a mixture containing approximately equal amounts of each of its enantiomers), or as an enantiomerically enriched mixture, in which one of its enantiomers is present in excess over the other. In a preferred embodiment, jasmonic acid is used as an enantiomerically enriched mixture containing at least 90% by weight of one of its enantiomers, and 10% by weight or less of the other of its enantiomers. More preferably, jasmonic acid is used as an enantiomerically enriched mixture containing at least 99% by weight of one of its enantiomers, and 1% or less of the other of its enantiomers. Even more preferably, jasmonic acid is used in enatiomerically pure form, i.e., as 100% by weight of one of its enantiomers.

In order to produce LCOs by the methods of the invention, the rhizobacteria cells are cultured in or on a culture medium containing the inducing compound. Suitable culture media and culture conditions are known in the art. For instance, yeast extract mannitol (YEM) medium, as exemplified herein, may be used. In order to obtain large quantities of LCOs, the rhizobacteria are preferably cultured in large-scale continuous liquid fermentation systems as are known and commercially available. Other culture conditions, such as aeration, agitation, temperature, etc. are not critical to the invention, and suitable culture conditions for growing rhizobacteria are known in the art.

The jasmonic acid, linoleic acid, linolenic acid or derivative thereof, or a combination of two or more thereof, is present in the culture medium at a concentration preferably in the range of about 10 to about 200 µM, more preferably about 25 to about 100 µM, and even more preferably about 50 µM.

Genistein may additionally be present in the culture medium at a concentration preferably in the range of about 1 to about 100 µm, more preferably about 1 to about 25 µM, and even more preferably about 5 µM.

As used herein, the term "about" means up to ±25% of the stated value. For instance, "about 50 µM" encompasses the range of 37.5 µM to 62.5 µM i.e. 50 µm ±25%.

Methyl jasmonate is a preferred inducing compound. In a particularly preferred embodiment, methyl jasmonate and genistein are both present in the culture medium.

The LCOs may be recovered from the culture medium by any suitable technique, the choice of which is not critical to the invention. For instance, high-performance liquid chromatography (HPLC), as exemplified in Example 1 herein, may be used.

Rhizobial inoculant compositions containing linoleic acid, linolenic acid, jasmonic acid, or derivatives thereof, or genistein, in amounts sufficient to induce LCO production by the rhizobacteria, and which are suitable for use for inoculating legume plants to promote nitrogen fixation, may be formulated in accordance with known techniques. Techniques for formulating inoculants are known in the art. Typically, inoculants are in a dried or liquid form. Dried inoculants (powdered peat inoculants) generally contain dried bacteria mixed with sterilized peat and then packaged. The inoculant may contain carriers, blending agents, extenders, excipients, adjuvants, et cetera, as are known in the art. The dried inoculant may also include a binding or sticking agent to help the bacteria adhere to the plant seeds, roots, etc. upon application. Liquid inoculants may be prepared by suspending the bacteria in a suitable diluent or carrier, such as water.

In an alternative embodiment, the rhizobial inoculant may not contain jasmonic acid, linoleic acid, linolenic acid or a derivative thereof. Instead, the rhizobacteria will previously have been grown in or on a culture medium containing jasmonic acid, linoleic acid, linolenic acid or a derivative thereof, whereby the beneficial effects of such compounds on nod gene induction or LCO production is obtained, and the rhizobacteria so produced are then formulated into a rhizobial inoculant.

The rhizobial inoculants of the invention are useful for increasing nitrogen fixation in all leguminous plants in which nitrogen fixation by rhizobacteria occurs. Non-limiting examples of legumes include soybeans, peanuts, all the pulses, including peas and lentils, all the beans, and major forage crops, such as alfalfa and clover. Legumes also include many more plants of lesser agricultural importance, such as lupines, sainfoin, trefoil, and even some small tree species.

Techniques for applying rhizobial inoculants to legumes are known in the art, including appropriate modes of administration, frequency of administration, dosages, et cetera. Typically, liquid or powdered compositions are applied to seeds, although the rhizobacteria composition may also be applied to soil, either before or after planting, or contemporaneously therewith. Any part of the plant may be inoculated, such as the roots, seeds, stems or leaves.

Inoculant compositions according to the invention are preferably applied to plants grown under conditions that result in an average daily root zone temperature of less than 25°, more preferably less than 20° C., 19° C., 18° C., 17° C., 16° C., 15° C., 14° C., 13° C., 12° C., 11° C. or 10° C., as may be found in many northerly climates. Average daily root zone temperature is calculated as the average 24-hour root zone temperature of the plant over the entire growing season, from the time of planting through to harvest. Alternatively, and where specifically indicated herein, average daily root zone temperature is calculated as the average 24-hour root zone temperature for a particular month, e.g. March, April, May, June, July, August, September or October.

Kits containing inoculants of the invention will typically include one or more containers of the inoculant, and printed instructions for using the inoculant for promoting plant growth. The kit may also include tools or instruments for reconstituting, measuring, mixing, or applying the inoculant, and will vary in accordance with the particular formulation and intended use of the inoculant.

Further details concerning the preparation of bacterial inoculants and methods for inoculating plants with bacterial inoculants are found in e.g. U.S. Pat. Nos. 5,586,411; 5,697,186; 5,484,464; 5,906,929; 5,288,296; 4,875,921; 4,828,600; 5,951,978; 5,183,759; 5,041,383; 6,077,505; 5,916,029; 5,360,606; 5,292,507; 5,229,114; 4,421,544; and 4,367,609, each of which is incorporated herein by reference.

Unless defined otherwise, all technical and scientific terms used herein are intended to have the same meaning as is commonly understood by one of ordinary skill in the relevant art.

As used herein, the singular forms "a," "an", and "the" include the plural reference unless the context clearly dictates otherwise.

The following examples are illustrative, but not limiting, of the present invention. Other suitable modifications and adaptations are of the variety normally encountered by those skilled in the art and are fully within the spirit and scope of the present invention.

EXAMPLE 1

Experiment 1

This experiment evaluated the effect of salicylates and fatty acids including jasmonic acid and its methyl ester, methyl jasmonate, and on the induction of nod genes in *Bradyrhizobium japonicum* strain USDA3.

Bacterial Strains

*Bradyrhizobium japonicum* strain USDA3, harboring plasmid GG4, was used in the experiment. Plasmid GG4 contains a translational fusion between *B. japonicum* nod Y open-reading frame and lac Z of *Escherichia coli*. Hence, the nod gene expression activity due to various inducers was indirectly measured by the amount of β-galactosidase activity.

Bacterial Growth and Incubation

Bacteria were grown in yeast extract mannitol (YEM) medium (mannitol 10.0 g, $K_2HPO_4$ 0.5 g, $MgSO_4.7H_2O$ 0.2 g, NaCl 0.1 g, and yeast extract 0.4 g dissolved in 1000 mL of dd $H_2O$). In order to ensure the maintenance of the strains, tetracycline was added to the bacterial cultures at a concentration of 20 mg $l^{-1}$. One hundred mL cultures of each strain, in 250 mL flasks, were shaken at 150 rev $min^{-1}$ at 30° C. for 3-5 days and then subcultured into 400 mL of fresh medium in 1000 mL flasks. The cultures were incubated until the $OD_{620}$ reached 0.2-0.3. The cultures were then divided into 5 mL tubes (sterilized).

Stock solutions of various inducers: genistein, salicylic acid and acetylsalicylic acid made in methanol and linolenic, linoleic, and jasmonic acid and methyl jasmonate were made in ethanol, and an appropriate amount of these inducers was added into the tubes before addition of bacterial culture. In the tubes, the final concentration of all the inducers was maintained as 5, 10, 25, 50 and 100 µM. Tubes were collected after 18 h of incubation and stored at −20° C. until the β-galactosidase activity was measured. Genistein (4',5,7, trihydroxyisoflavone, purity 98%,), linolenic acid (9,12,15-Octadecatrienoic acid, purity 99%), linoleic acid (cis-9, cis-12-Octadecadienoic acid, purity 99%), jasmonic acid (±Jasmonic acid, $C_{12}H_{18}O_3$) and salicylic acid (2-hydroxybenzoic acid, purity 99.0%) were obtained from Sigma, while acetylsalicylic acid ($C_9H_8O_4$, 99% purity) was obtained from Acros and methyl jasmonate (95% purity) was obtained from Aldrich Chemical Company, Inc.

β-Galactosidase Activity Assay

β-galactosidase is an enzyme which hydrolyzes β-D-galactosides. The activity of this enzyme can easily be measured with colorless substrates, which upon hydrolysis produce colored products. O-nitrophenyl-β-galactoside (ONPG) is a colorless compound and is converted to galactose and O-nitrophenol in the presence of β-galactosidase. The O-nitrophenol is yellow and can be measured by its absorption at 420 nm. In the present study, nod gene expression was indirectly measured by β-galactosidase activity following the method of Miller (1972) as modified by Stachel et al, (1985). Briefly, 0.5 mL culture was mixed with 2×Z buffer ($Na_2HPO_4.7H_2O$, 16.1 g, $NaH_2PO_4.H_2O$, 5.5 g, KCl 0.75 g, $MgSO_4.7H2O$ 0.246 g, β-mercaptoethanol 2.7 g, pH 7.0 dissolved in 500 mL water) and 40 µL toluene and vortexed for 10 seconds. The culture was then incubated in a water bath at 37° C. for 30 minutes and then 0.2 mL of O-nitrophenyl β-D-galactopyranoside (ONPG) was added at a concentration of 4 mg $mL^{-1}$. The cultures were incubated again in the water bath until the color of the culture changed. The reaction time was recorded and the reaction was stopped with 1M $Na_2CO_3$. After centrifugation at 10,000 rpm for 4 minutes, spectrophotometric reading at $OD_{420}$ and $OD_{600}$ were taken and the β-galactosidase activity was measured (β-galactosidase activity=$OD_{420}$*1000/$OD_{600}$*T*V, where T is the reaction time and V is the volume of the bacterial culture used for enzyme assay).

Statistical Analysis

The experiment was designed in a randomized complete block design (RCBD) with three replicates. The experiment was run two times and the results were similar in both the cases. Data are shown from the second experiment. Statistical analysis of the data was done with analysis of variance using the Statistical Analysis System computer package (SAS Institute, 1988). Comparisons among treatment means were made with an ANOVA protected LSD at the 0.05 level of statistical significance.

Experiment 2

This experiment was conducted to evaluate the effect of jasmonates on the production of lipo-chito oligosaccharides (LCOs) from *Bradyrhizobium japonicum* USDA 3.

Bacterial Culture and Incubation

*Bradyrhizobium japonicum* (strain USDA 3) was grown at 28° C. in yeast extract mannitol medium (YEM) (mannitol 10 g, $K_2HPO_4$ 0.5 g, $MgSO_4.7H_2O$ 0.2 g, NaCl 0.1 g, yeast extract 0.4 g, and distilled water 1000 ml), pH 6.8, shaken at 150 rpm until the $OD_{620}$ reached 0.4-0.6 (4-6 d) in the dark. Thereafter, 2.0 l of bacterial subculture was started by inoculating with material from the first culture (5 ml of the first culture per 250 ml of YEM media), until the $OD_{620}$ reached to 0.2-0.4. At this stage, methyl jasmonate, jasmonic acid and genistein were added to culture so that the final concentraton for methyl jasmonate and jasmonic acid was 5, 10, 25, 50 and 100 µM and 5 µM for genistein. The culture was incubated for 48-96 h and the LCO extracted according to the following procedure.

Extraction and Purification of LCO

The LCO from the induced bacterial culture was isolated with XAD resins. Before using XAD resins for extraction, they were first conditioned. Each 40 grams of XAD resins were first washed two times with 20 mL acetone after conditioning for 15 minutes. This was followed by two washes of 20 mL methanol when the resins were conditioned for 15 minutes. Finally, the XAD resins were conditioned (5 min) and washed with 20 mL dd. water two times. The conditioned resins were placed in the refrigerator at 4° C. until use.

For each one liter of bacterial culture, 40 grams of resin was added to the flask and these were shaken together overnight at 150 rpm. The culture along with the resin was poured through a funnel into a flask fitted with a course brass mesh (fine enough to allow the culture go quickly through and filter out the resin without any loss). At this stage, the resins are washed with water. In order to extract LCO from the resin, the XAD resin was passed through a vacuum filtration system. The fritted glass base of the system was fitted with Whatman #1 paper disk with the objective to keep the solvent with the bead until vacuum is applied. The resin beads were washed two times with 40 mL methanol after conditioning for 5 minutes. After this, the beads were again washed two times with 30 mL acetone after conditioning for 15 minutes. The filtrate of the methanol and acetone washes was collected and transferred to a 250 mL boiling flask and placed on a rotary evaporator (Yamota RE500, Yamato, USA) operated at 45° C. and a speed of 125 rpm. Evaporation was continued until the flask became dry. The extract was then resuspended in 4 ml of 18% acetonitrile and kept in the dark at 4° C. in a sealed glass vial, until use.

HPLC (equipped with Waters Model 510 HPLC pump, Waters model 712 WISP and Waters model 410 differential refractometer, Waters, Mass., USA) analysis was conducted with a Vydac C18 reversed-phase column (Vydac, Calif., USA; catalogue no. 218TP54) with a flow rate of 1.0 ml min$^{-1}$ and a Vydac guard column (catalogue no. 218GK54). As a baseline 18% acetonitrile (AcN/H$_2$O; w/w) was run through the system for at least 10 min. prior to sample injection. The sample was loaded and isocratic elution was conducted with 18% of AcN for 45 min to remove all non-polar light fractions. Thereafter, gradient elution was conducted for 90 min with 18-82% AcN. The LCO eluted at 94-96 min of HPLC run time.

Biological Activity of LCO (Root Hair Deformation Assay)

Biological activity of a compound is an important step to confirm its activity. LCOs are signal molecules that induce root hair curling in host plants. We tested the biological activity of MeJA induced LCO in soybean roots and found root hair curling (HAC) and deformation (HAD) in soybean root segments in a fashion similar to that demonstrated by genistein induced LCO production. Root hair deformation was studied according to the procedure of Prithiviraj et al (2000). Seeds of soybean (cultivars: AC Bravor, OAC Brussels, Maple Glen, Nordet, cv. 9007) were surface-sterilized with 2% sodium hypochlorite for 2 min. followed by four washes of sterile distilled water. The seeds were then placed on 1.5% water agar (20 ml) in 9 cm diameter Petri dishes (two seeds per plate). The Petri dishes were incubated in the dark at 25° C. for 7-8 d; so that the seeds germinated and developed tap and lateral roots on the agar surface. Lateral roots with abundant root hairs were excised and placed on sterile grease-free glass slides containing 40-60 µl of LCO solution. The slides were incubated in a closed moist chamber at 25° C. in the dark and after 24 h of incubation time, the slides were removed, the roots were fixed in a staining solution [methylene blue (0.02% w/v)+glycerol (20% v/v)+phenol (10% w/v)]. Light microscopic studies were observed for root hair deformation of the jasmonic acid, methyl jasmonate and genistein induced LCO. Each treatment had three replicate lateral roots, and a minimum of 100 root hairs was observed from each replicate.

Results

Genistein and diadzein are produced naturally from legume roots and induce the expression of nod genes in *Bradyrhizobium japonicum*. Here we studied the possible effect of various other compounds, salicylates (salicylic and acetylsalicylic acid) and fatty acids (linolenic and linoleic acid) including jasmonic acid and its methyl ester, methyl jasmonate on the induction of nod genes in *B. japonicum* USDA3. Genistein, the natural inducer of nod genes, was used a positive control since genistein is a stronger inducer of nod gene in *B. japonicum* than diadzein.

Our results with β-galactosidase assay showed that jasmonic acid (JA) and methyl jasmonate (MeJA) strongly induced the expression of nod genes at concentrations from 25 to 100 µM (FIG. 1). However, methyl jasmonate showed maximum induction of nod genes, as compared to jasmonic acid, at the optimum genistein concentration (5 µM). At concentrations 10 µM or less, jasmonic acid as well as methyl jasmonate showed no activity (FIG. 1).

Figure 6:
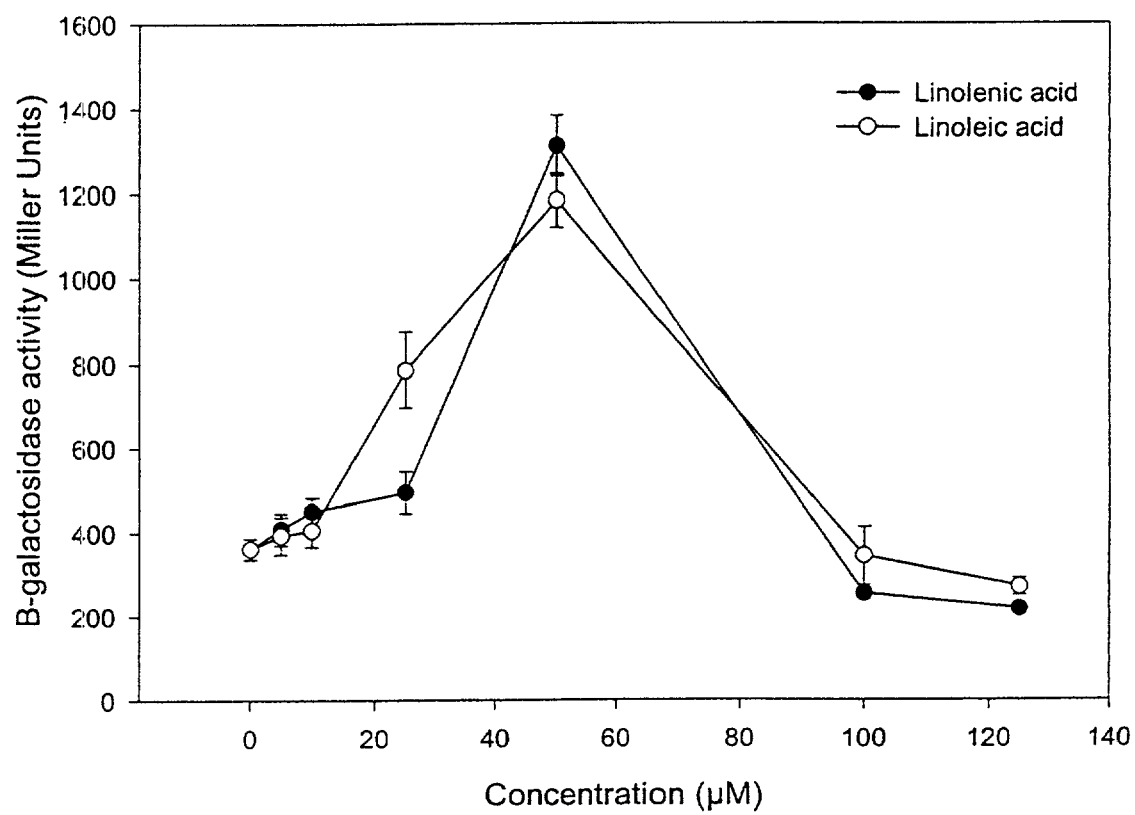
FIG. 6 is a graph depicting the effect of linolenic and linoleic acid on the induction of nod genes in *Bradyrhizobium japonicum* strain USDA3 as measured by β-galactosidase activity (Miller Units).

Linolenic and linoleic acid also induced the expression of nod genes with 50 µM as the optimum concentration (FIG. 6). However, nod gene induction due to linolenic and linoleic acid, at their optimum concentrations, was lower than the optimum JA and MeJA concentrations.

On the other hand, salicylates (salicylic acid and acetylsalicylic acid) did not show any activity on the induction of nod genes; the β-galactosidase activity was not different from the control (without any inducer) at all concentrations (FIG. 1).

In order to study the possible interactions among genistein and various other compounds, various combinations of jasmonic acid, methyl jasmonate, salicylic acid, acetylsalicylic acid and genistein were tested and the β-galactosidase activity estimated. The optimum level of genistein (5 µM) and equimolar combinations of JA, MeJA, SA and ASA at 25 and 50 µM concentrations were used.

Figure 2:
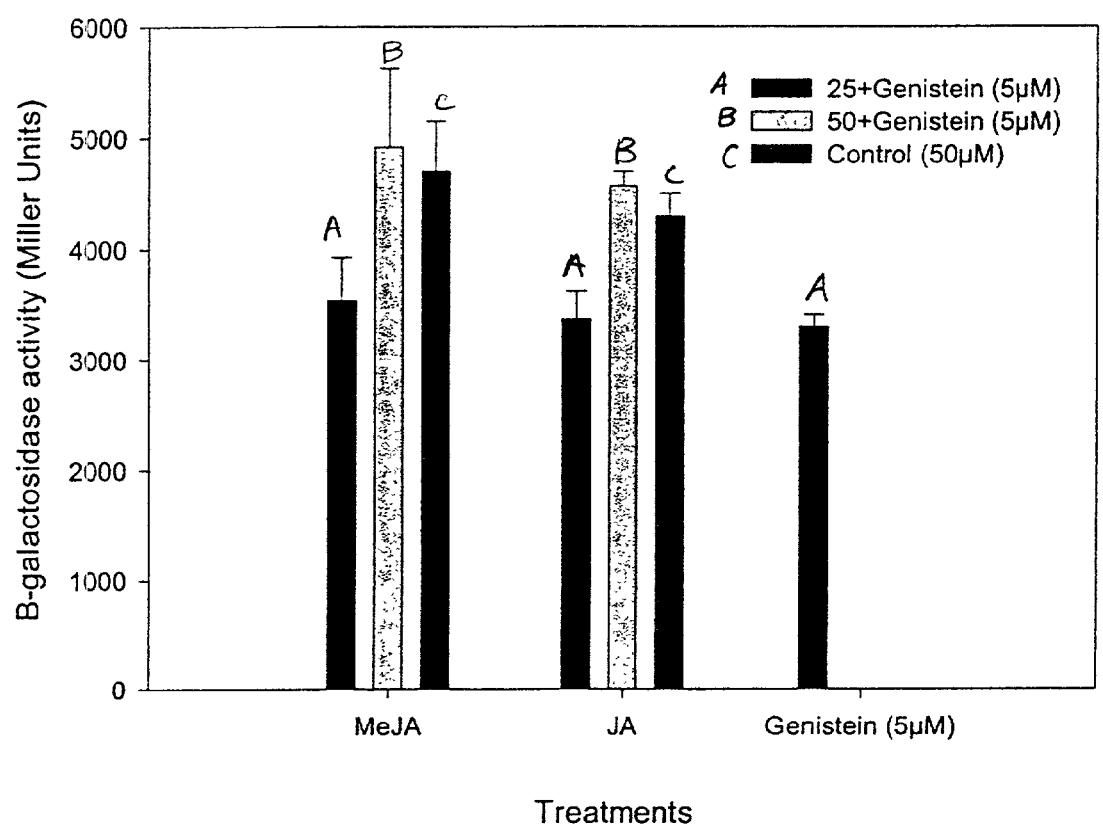
FIG. 2 is a graph depicting the effect of genistein with the addition of jasmonic acid and methyl jasmonate on the induction of nod genes in *Bradyrhizobium japonicum* strain USDA3 as measured by β-galactosidase activity (Miller Units).

The results showed that simultaneous addition of genistein with either JA or MeJA at various concentrations did not result in any synergistic effect when β-galactosidase activity was measured (FIG. 2). SA and ASA did not show any activity alone, and in order to study their interaction with other inducers, both SA and ASA were tested at two concentrations (25 and 50 µM) with JA, MeJA and genistein (at 5 µM, the optimum level for nod gene induction by genistein).

Figure 3:
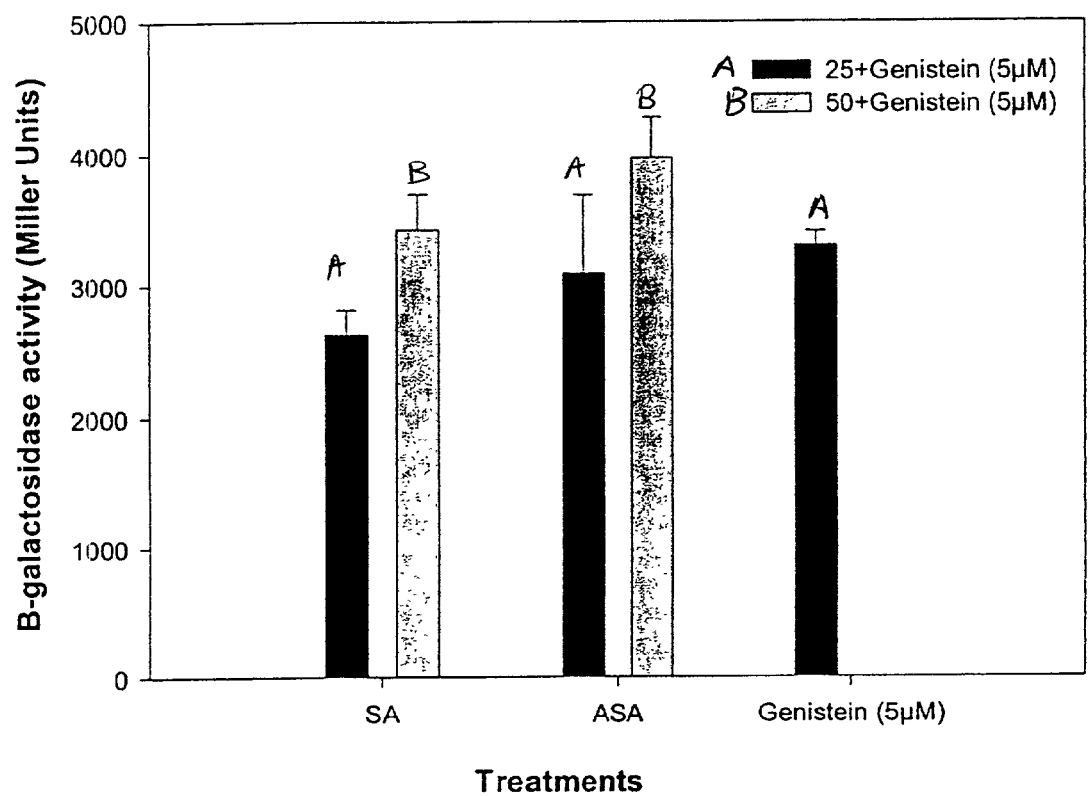
FIG. 3 is a graph depicting the effect of genistein with the addition of salicylic acid and acetylsalicylic acid on the induction of nod genes in *Bradyrhizobium japonicum* strain USDA3 as measured by β-galactosidase activity (Miller Units).
Figure 4:
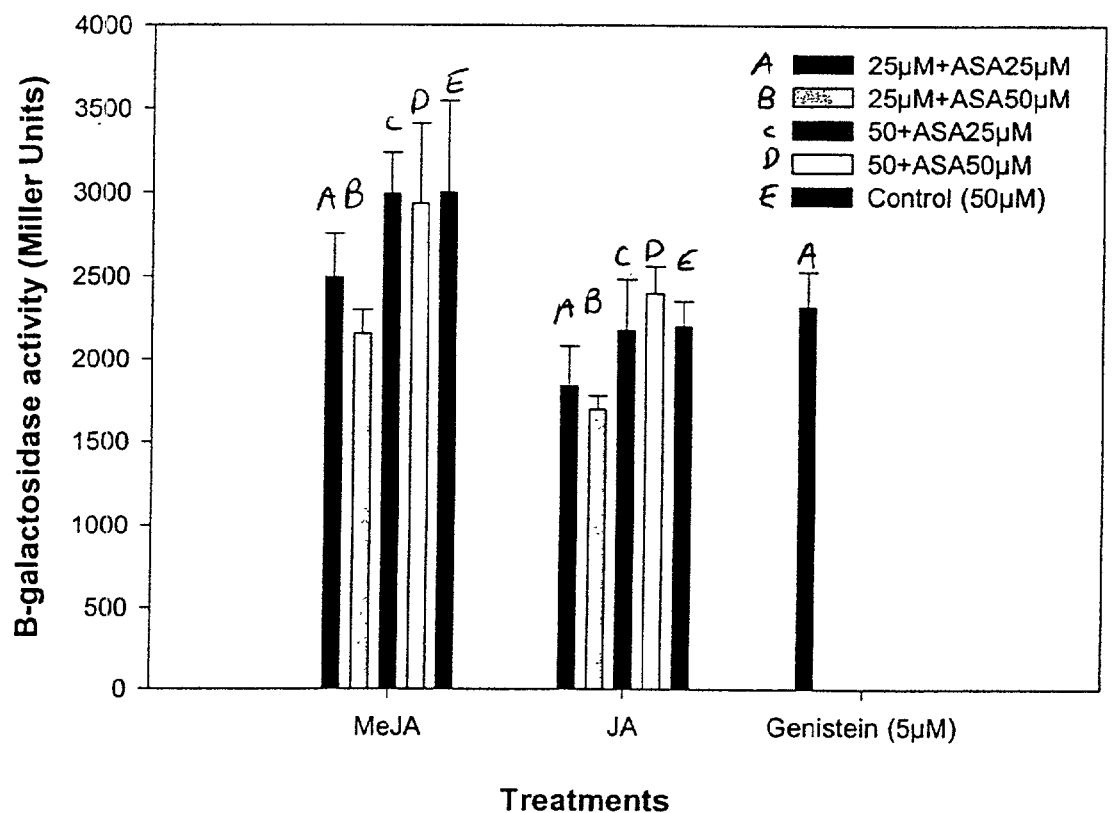
FIG. 4 is a graph depicting the effect of genistein with the addition of methyl jasmonate, jasmonic acid, and salicylic acid on the induction of nod genes in *Bradyrhizobium japonicum* strain USDA3 as measured by β-galactosidase activity (Miller Units).
Figure 5:
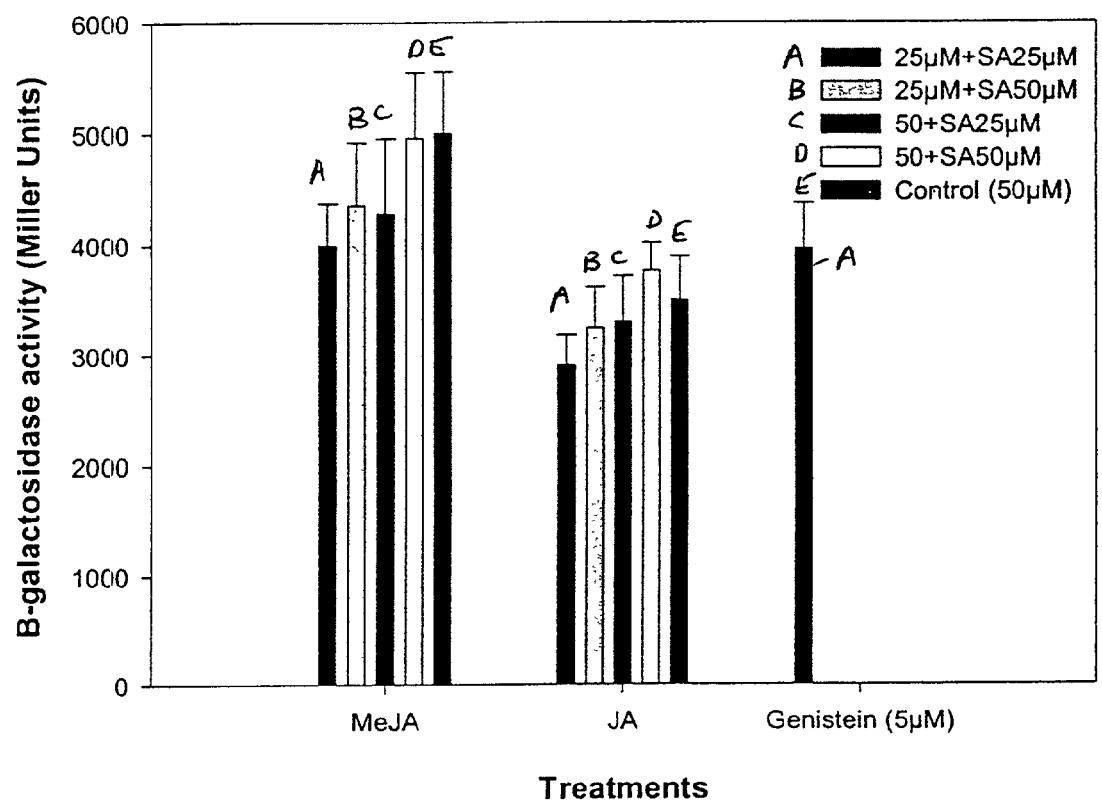
FIG. 5 is a graph depicting the effect of genistein with the addition of methyl jasmonate, jasmonic acid, and acetylsalicylic acid on the induction of nod genes in *Bradyrhizobium japonicum* strain USDA3 as measured by β-galactosidase activity (Miller Units).

In all the combinations studied, both SA and ASA did not show inhibitory or inducing activity, when analyzed by β-galactosidase assay (FIGS. 3, 4, and 5).

The β-galactosidase assay indirectly measures the transcription of nod genes, and in order to measure the end product of nod gene expression [lipo-chito oligosaccharides—LCOs], wild type USDA3 strain were induced with JA, MeJA and genistein (as a positive control) and LCO was isolated. Both JA and MeJA, at optimum concentrations, induced the production of LCOs. MeJA induced *B. japonicum* to produce more LCO and at the 100 µM concentration, MeJA induced substantially more LCO than the optimum genistein concentration (5 µM).

EXAMPLE 2

This experiment was conducted to evaluate nod gene induction by jasmonates in various *Bradyrhizobium japonicum* strains.

The effect of 0-100 μM concentrations of each of acetylsalicylic acid, salicylic acid, jasmonic acid, methyl jasmonate, and genistein, on induction of nod gene expression in *Bradyrhizobium japonicum* strains USDA31, USDA76, USDA121, and USDA3, was evaluated in accordance with the β-galactosidase assay of Experiment 1 in Example 1 above.

As shown in Table 1, induction of nod gene expression by jasmonic acid and methyl jasmonate was much greater in strain USDA3 than in the other strains tested, particularly at concentrations of jasmonic acid or methyl jasmonate between 25-100 μM. Moreover, methyl jasmonate had a substantially greater inducing effect than jasmonic acid.

reached this stage, it was divided equally into four flasks (150 mL) and specific concentrations of JA and genistein were added to the cultures.

One hundred and fifty mL of each culture were extracted with 40 mL of the HPLC-grade butanol (Fisher Science Ltd., 112 Colonnade Road, Nepean, ON, Canada) by shaking together for 5 minutes. The two phases were then allowed to separate by leaving the mixture to stand overnight. The upper layer (butanol) was collected with a glass pipette and 25 mL were placed in a 250 ml evaporation flask. LCO extract solutions were stored at 4° C. until evaporation. This step was conducted at 80° C. with a Yamato RE 500 Rotary Evaporator (Yamato Scientific American Inc., Orangeburge, N.Y., USA). The butanol phase was evaporated down to 2 to 3 mL. The resulting light brown material was dissolved in 4 ml of 18% acetonitrile and stored in the dark at 4° C. in a glass tube sealed with parafilm.

TABLE 1

Differential nod gene induction response of *Bradyrhizobium japoniucm* strains to jasmonates

| Conc. (μM) | ASA | SA | JA | MeJA | GEN |
|---|---|---|---|---|---|
| USDA31 (GG1) | | | | | |
| 0 | 522.6 ± 15.9 | 522.6 ± 15.9 | 522.6 ± 15.9 | 522.6 ± 15.9 | 522.6 ± 15.9 |
| 5 | 636.5 ± 66.9 | 587 ± 66.6 | 1653.3 ± 105.2 | 472.2 ± 14.8 | 2283.8 ± 57.7 |
| 10 | 563.3 ± 37.9 | 536.4 ± 40.1 | 2079 ± 254.9 | 485.3 ± 42.5 | 2007.6 ± 36.7 |
| 25 | 719.5 ± 75.2 | 522.4 ± 65.3 | 1853.3 ± 314.5 | 403.3 ± 5.6 | 1821 ± 89.2 |
| 50 | 676.6 ± 85.8 | 476.1 ± 28.4 | 1884.3 ± 289.3 | 500.1 ± 32 | 1121.1 ± 156.9 |
| 100 | 384.8 ± 34.4 | 519.3 ± 43.5 | 796 ± 67.3 | 392.9 ± 22.7 | 491.9 ± 31.6 |
| USDA 76 (GG2) | | | | | |
| 0 | 411.8 ± 26.8 | 411.8 ± 26.8 | 411.8 ± 26.8 | 411.8 ± 26.8 | 411.8 ± 26.8 |
| 5 | 363.2 ± 34.1 | 562.2 ± 26.6 | 393.5 ± 30.5 | 435.4 ± 39 | 1421.7 ± 93.4 |
| 10 | 341 ± 21.1 | 411.8 ± 75.3 | 447.9 ± 21 | 418.4 ± 53.1 | 1320.8 ± 75.99 |
| 25 | 418.8 ± 59.5 | 473 ± 58.3 | 420.1 ± 4.6 | 392.7 ± 2.1 | 1383.8 ± 98.22 |
| 50 | 376.2 ± 37.2 | 464.6 ± 36.2 | 375.1 ± 35.3 | 410.4 ± 24.5 | 1160.7 ± 89.7 |
| 100 | 413.1 ± 85.5 | 430.7 ± 55.3 | 357.7 ± 9.7 | 386.4 ± 37.3 | 413.7 ± 7.4 |
| USDA121 (GG3) | | | | | |
| 0 | 476.8 ± 86.6 | 476.8 ± 86.6 | 476.8 ± 86.6 | 476.8 ± 86.6 | 476.8 ± 86.6 |
| 5 | 422.6 ± 64.9 | 404.1 ± 62.5 | 540.3 ± 79.3 | 518 ± 42.6 | 2081.7 ± 148.5 |
| 10 | 425 ± 39.4 | 472.7 ± 54.3 | 473.7 ± 58.3 | 487.1 ± 33 | 1685.1 ± 53.3 |
| 25 | 479.9 ± 88.6 | 435.8 ± 69.2 | 496 ± 49.2 | 427 ± 29.4 | 1286.8 ± 145.5 |
| 50 | 445.4 ± 99 | 434.2 ± 26.3 | 412.7 ± 22.9 | 549.2 ± 81.6 | 1154.5 ± 121.1 |
| 100 | 325.6 ± 58.8 | 369.8 ± 114.9 | 329.5 ± 19.3 | 487.9 ± 89.3 | 430.9 ± 80.6 |
| USDA3 (GG4) | | | | | |
| 0 | 362 ± 25 | 362 ± 25 | 362 ± 25 | 362 ± 25 | 362 ± 25 |
| 5 | 396 ± 14.7 | 398 ± 13 | 368 ± 23 | 448 ± 30 | 3304 ± 333 |
| 10 | 372 ± 16 | 402 ± 33 | 362 ± 9 | 500 ± 61 | 2500 ± 94 |
| 25 | 382 ± 16 | 414 ± 17 | 3200 ± 230 | 3000 ± 350 | 2300 ± 219 |
| 50 | 464 ± 7 | 435 ± 26 | 3900 ± 150 | 4700 ± 450 | 1930 ± 74 |
| 100 | 527 ± 36 | 515 ± 583 | 550 ± 210 | 4500 ± 400 | 406 ± 15 |

Legends:
ASA Acetylsalicylic acid
SA Salicylic acid
JA Jasmonic acid
MeJA Methyl jasmonate

EXAMPLE 3

This example illustrates that jasmonic acid (JA) can prevent the inhibition of LCO production under low temperature, and that JA enhances the ability of genistein to induce LCO production.

Cultures of *B. japonicum* (strain USDA 110) were grown at 28° C. in 600 ml of sterile yeast mannitol medium (YEM) at pH 6.8. The culture was shaken at 150 rpm until an $OD_{620}$ of 0.4 to 0.6 was achieved (4 to 6 days). When the culture For HPLC analysis we used a Vydac C18 reversed—phase column (VYDAC, Hesperia, Calif., USA) with a flow rate of 1.0 mL/min and a Vydac guard column (VYDAC, Hesperia, Calif., USA). We used at least 10 min. of isocratic run with 18% acetonitrile (AcN/$H_2O$; w/w) to establish a baseline. The baseline value was always about 0.010. When a sample was loaded we conducted an isocratic elution with 18% AcN for 45 min. This step removed all non-polar light fractions. We then applied a gradient elution (18 to 82% AcN) for 70 min. LCOs begin to appear at 84 to 86 min of HPLC run time. We used B. japonicum Nod factor (BjV (C$_{18:1}$, MeFuc)) obtained from G. Stacey (University of Tennessee, Knoxville, Tenn.) as a standard. The identity of the LCO was confirmed by the Complex Carbohydrate Research Center at the University of Georgia with FAB-MS and MALDI-TOF spectrometry analysis.

There were two experiments conducted. In the first the treatments consisted of factorial combinations of two concentrations (0 and 20 μM) of two signal materials (JA and genistein (zhang and Smith, 1995)). The experiment was organized following a randomized complete block design with three blocks. In experiment 1, two temperatures were used (17 and 25° C.). The LCO was extracted 10 h after the addition of the signal compounds. Experiment 2 was generally like experiment one except that only one temperature, 17° C. was used and LCO was extracted at 5, 10, 20 hour after JA and genistein were added.

Each of the above experiments was conducted two times and the experimental results were pooled and analyzed statistically by analysis of variance using the Statistical Analysis System computer package (SAS Institute Inc. 1980). A least significant difference (LSD) test was applied to make comparisons among the means at the 0.05 level of significance, when analysis of variance showed significant treatment effects. Since the effects of temperature on growth were very large, the data from two temperatures used in the first experiment were analyzed separately.

Our data showed that JA can improve LCO production at a low temperature (17° C.) but not at 25° C. However, JA alone can not promote LCO production by B. japonicum USDA 110 at either temperature; genistein must be present (Table 2). There was no statistical interaction between levels of the JA and genistein factors.

We suppose that at low temperatures B. japonicum needs additional signal compounds, which come in the form JA. When JA was supplied in addition to genistein, it helped to prevent the low temperature inhibition of B. japonicum LCO production. Previous studies suggest that under at least some stresses (low temperature (17° C.) and pathogen infection) and for higher levels of nodulation under low temperature stress, the biosynthesis of JA in plants is a necessary response. But under optimum temperature conditions the biosynthesis of JA may not be required for soybean nodulation because we found that JA did not improve LCO production by B. japonicum under these conditions. At low temperatures it is probable that some gene is activated by application of JA and produces a product that improves the action of genistein on LCO production. The stimulation of LCO production by JA is important because we found that higher concentrations of genistein inhibit LCO production in our previous experiments (unpublished data) placing an upper limit on the amount of improvement in inoculum efficacy that can be achieved by genistein addition.

Our previous experimental work (unpublished data) and the findings reported here indicate that the peak-time for LCO production is around 8-10 hours after the genistein was added to the cell culture (Table 3). It is interesting to note that stimulation of LCO production by JA was apparent after 5 to 10 h. We did not find any difference in LCO production between JA at 20 μM plus genistein at 0 μM and JA at 20 μM and genistein at 20 μM at 20 hour (Table 3). We do not know why LCO production by B. japonicum at 20 h is less than at 10 h with genistein and JA, but it may be that the soybean—B. japonicum system does not need additional LCO and degrades it, or that The LCO has been changed to other compounds involved in on, reducing the LCO content.

In summary, we found that JA can help genistein promote LCO production by B. japonicum USDA 110 under low temperature, but JA cannot initiate LCO production in the absence of genistein.

TABLE 2

The effects of jasmonic acid and genistein concentration on LCO production by B. japonicum USDA 110 at 17 and 25° C. **, NS indicates differences at the 0.05 probability level, and not significant at P < 0.11 respectively.

| Factors | | LCO production (μg cell-1) | |
|---|---|---|---|
| JA concentration (μM) | Genistein concentration (μM) | 17° C. | 25° C. |
| 0 | 0 | 0 | 0 |
| 0 | 20 | 236 | 439 |
| 20 | 0 | 0 | 0 |
| 20 | 20 | 321 | 451 |
| LSD$_{0.05}$ | | 78 | 152 |
| JA | | ** | NS |
| Genistein | | ** | ** |
| JA × Genistein | | NS | NS |

TABLE 3

The effects of jasmonic acid and genistein concentration on the change of LCO production by B. japonicum USDA 110 with the time of addition to the culture. **, NS indicates differences at the 0.05 probability level.

| Factors | | LCO production (μg cell-1) | | |
|---|---|---|---|---|
| JA concentration (μM) | Genistein concentration (μM) | 5 hour | 10 hour | 20 hour |
| 0 | 0 | 0 | 0 | 0 |
| 0 | 20 | 113 | 493 | 88 |
| 20 | 0 | 0 | 0 | 0 |
| 20 | 20 | 201 | 1046 | 81 |
| LSD$_{0.05}$ | | 57 | 268 | 39 |
| JA | | ** | ** | NS |
| Genistein | | ** | ** | ** |
| JA × Genistein | | NS | NS | NS |

REFERENCES

Miller, J. 1972. Experiments in Molecular Genetics, pp. 352-355. Cold Spring Harbor Laboratory, Cold Spring Harbor, N.Y.

Prithiviraj, B., X. Zhou, A. Souleimanov, and D. L. Smith. 2000. Differential response of soybean [Glycine maz (L.) Merr.] genotypes to lipo-chito-oligosaccharide Nod Bj V (C18:1 MeFu). Jour. Exp. Botany. 51: 2045-2051.

Rosas, S., R. Soria, N. Correa, and G. Abdala. 1998. Jasmonic acid stimulates the expression of nod genes in Rhizobium. Plant Mol. Biol. 38: 1161-1168.

Smith, D. L., and Hume, D. J. 1987. Comparison of assay methods for N2 fixation utilizing white bean and soybean. Can. J. Plant Sci. 67:11-19.

Stachel, S. E., G. An, C. Flores, and E. W. Nester. 1985. The Tn3-LacZ transposon for the random generation of beta-galactosidase gene fusion: application to the analysis of gene expression in Agrobacterium. EMBO Jour. 4: 891-898.

Zhang, F., Charles, T. V., Pan, B., Smith, D. L. 1996. Inhibition of the expression of B. japonicum nod genes at low temperatures. Soil Biol. Biochem. 28:1579-1583.

Zhang, F., and Smith, D. L. 1996. Inoculation of soybean (Glycine max (L.) Merr.) with genistein-preincubated *Bradyrhizomium japonicum* or genistein directly applied into soil ncreases soybean protein and dry matter yield under short season conditions. Plant Soil 179:233-241.

Zhang, F., Smith, D. L. 1995. Preincubation of *Bradyrhizobium japonicum* with genistein accelerates nodule development of soybean [Glycine max (L.) Merr.] at suboptimal root zone temperatures. Plant Physiol. 180:961-968.

All patents and publications cited herein are hereby fully incorporated by reference in their entirety, and are illustrative of the level of skill in the art to which this invention pertains. The citation of any publication is for its disclosure prior to the filing date and should not be construed as an admission that the present invention is not entitled to antedate such publication by virtue of prior invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

The invention claimed is:

1. A method for promoting nitrogen fixation by soybean plants, comprising:
   inoculating a soybean plant with a rhizobial inoculant, wherein said rhizobial inoculant comprises rhizobacteria of the species *Bradyrhizobium japonicum*, and at least one compound selected from the group consisting of: jasmonic acid or an ester or salt thereof; linoleic acid or an ester or salt thereof; and linolenic acid or an ester or salt thereof.

2. The method according to claim 1, wherein said inoculating comprises applying said rhizobial inoculant to said plant, or to a part, seed or root thereof, or to soil adjacent thereto.

3. The method according to claim 2, wherein said inoculating comprises applying said rhizobial inoculant to said soil prior to planting.

4. The method according to claim 1, further comprising growing said plants under conditions that result in an average daily root zone temperature of less than 25° C.

5. The method according to claim 1, wherein said at least one compound comprises jasmonic acid or an ester or salt thereof.

6. The method according to claim 1, wherein said at least one compound comprises an ester of jasmonic acid.

7. The method according to claim 1, wherein said at least one compound comprises methyl jasmonate.

8. The method according to claim 1, wherein said at least one compound comprises jasmonic acid.

9. The method according to claim 4, wherein said average daily root zone temperature is less than 20° C.

10. The method according to claim 4, wherein said average daily root zone temperature is less than 17° C.

11. The method according to claim 4, wherein said average daily root zone temperature is less than 15° C.

12. The method according to claim 4, wherein said average daily root zone temperature is less than 13° C.

13. The method according to claim 4, wherein said average daily root zone temperature is less than 10° C.

14. The method according to claim 1, wherein said rhizobial inoculant is in a dried or liquid form.

15. The method according to claim 1, wherein said rhizobial inoculant comprises a carrier, blending agent, extender, excipient, or adjuvant.

16. A rhizobial inoculant for promoting nitrogen fixation by soybean plants, said rhizobial inoculant comprising rhizobacteria of the species *Bradyrhizobium japonicum*, and at least one compound selected from the group consisting of: jasmonic acid or an ester or salt thereof; linoleic acid or an ester or salt thereof; and linolenic acid or an ester or salt thereof.

17. The rhizobial inoculant according to claim 16, wherein said at least one compound comprises jasmonic acid or an ester, or salt thereof.

18. The rhizobial inoculant according to claim 16, wherein said at least one compound comprises jasmonic acid.

19. The rhizobial inoculant according to claim 16, wherein said at least one compound comprises an ester of jasmonic acid.

20. The rhizobial inoculant according to claim 16, wherein said at least at least one compound comprises methyl jasmonate.

* * * * *